(12) United States Patent
Kehoskie et al.

(10) Patent No.: US 7,422,559 B2
(45) Date of Patent: Sep. 9, 2008

(54) BORESCOPE COMPRISING FLUID SUPPLY SYSTEM

(75) Inventors: Michael P. Kehoskie, Auburn, NY (US); Thomas W. Karpen, Skaneateles, NY (US); Allan I. Krauter, Skaneateles, NY (US); Raymond A. Lia, Auburn, NY (US); Bradford Morse, Syracuse, NY (US); Kenneth Von Felten, Freeville, NY (US)

(73) Assignee: GE Inspection Technologies, LP, Lewiston, PA (US)

( * ) Notice: Subject to any disclaimer, the term of this patent is extended or adjusted under 35 U.S.C. 154(b) by 588 days.

(21) Appl. No.: 10/869,822

(22) Filed: Jun. 16, 2004

(65) Prior Publication Data

US 2005/0281520 A1   Dec. 22, 2005

(51) Int. Cl.
*A61B 1/005* (2006.01)
*G01N 21/00* (2006.01)
*H04N 7/18* (2006.01)

(52) U.S. Cl. .......... 600/140; 600/156; 348/82; 356/241.4

(58) Field of Classification Search .......... 600/139, 600/140, 156, 157; 348/82–85; 356/241.1, 356/241.5, 241.4
See application file for complete search history.

(56) References Cited

U.S. PATENT DOCUMENTS

| 4,006,486 A | 2/1977 | Vaughn et al. |
| 4,279,245 A * | 7/1981 | Takagi et al. .......... 600/139 |
| 4,301,790 A | 11/1981 | Bol et al. |
| 4,562,473 A * | 12/1985 | Levine .......... 348/244 |
| 4,700,693 A | 10/1987 | Lia et al. |
| 4,711,524 A | 12/1987 | Morey et al. |
| 4,727,859 A | 3/1988 | Lia |
| 4,733,937 A | 3/1988 | Lia et al. |
| 4,735,501 A | 4/1988 | Ginsburgh et al. |
| 4,787,369 A | 11/1988 | Allred, III et al. |
| 4,790,294 A | 12/1988 | Allred, III et al. |
| 4,794,912 A | 1/1989 | Lia |
| 4,796,607 A | 1/1989 | Allred, III et al. |
| 4,853,774 A | 8/1989 | Danna et al. |
| 4,862,253 A | 8/1989 | English et al. |
| 4,887,154 A | 12/1989 | Wawro et al. |
| 4,909,600 A | 3/1990 | Ciarlei et al. |
| 4,913,369 A | 4/1990 | Lia et al. |

(Continued)

FOREIGN PATENT DOCUMENTS

DE   2641594   3/1977

(Continued)

OTHER PUBLICATIONS

International Search Authority, International Search Report and Written Opinion, Oct. 5, 2005, 14 pages.

(Continued)

*Primary Examiner*—John P Leubecker
(74) *Attorney, Agent, or Firm*—GE Global Patent Operation

(57) ABSTRACT

A borescope device having an insertion tube, a camera head assembly, and a fluid supply system. The camera assembly includes through holes allowing fluid escape. The fluid supply system is controllable to force fluid through the through holes. The fluid supply system may be actuated to cool the camera head assembly.

21 Claims, 6 Drawing Sheets

U.S. PATENT DOCUMENTS

| | | | |
|---|---|---|---|
| 4,941,454 | A | 7/1990 | Wood et al. |
| 4,941,456 | A | 7/1990 | Wood et al. |
| 4,980,763 | A | 12/1990 | Lia |
| 4,989,581 | A | 2/1991 | Tamburrino et al. |
| 4,998,182 | A | 3/1991 | Krauter et al. |
| 5,018,436 | A | 5/1991 | Evangelista et al. |
| 5,018,506 | A | 5/1991 | Danna et al. |
| 5,019,121 | A | 5/1991 | Krauter |
| 5,047,848 | A | 9/1991 | Krauter |
| 5,052,803 | A | 10/1991 | Krauter |
| 5,061,995 | A | 10/1991 | Lia et al. |
| 5,066,122 | A | 11/1991 | Krauter |
| 5,070,401 | A | 12/1991 | Salvati et al. |
| 5,114,636 | A | 5/1992 | Evangelista et al. |
| 5,140,975 | A | 8/1992 | Krauter |
| 5,191,879 | A | 3/1993 | Krauter |
| 5,202,758 | A | 4/1993 | Tamburrino |
| 5,203,319 | A | 4/1993 | Danna et al. |
| 5,275,152 | A | 1/1994 | Krauter et al. |
| 5,278,642 | A | 1/1994 | Danna et al. |
| 5,314,070 | A | 5/1994 | Ciarlei |
| 5,323,899 | A | 6/1994 | Strom et al. |
| 5,333,603 | A | 8/1994 | Schuman |
| 5,345,339 | A | 9/1994 | Knieriem et al. |
| 5,347,989 | A | 9/1994 | Monroe et al. |
| 5,365,331 | A | 11/1994 | Tamburrino et al. |
| 5,373,317 | A | 12/1994 | Salvati et al. |
| D358,471 | S | 5/1995 | Cope et al. |
| 5,435,296 | A | 7/1995 | Vivenzio et al. |
| 5,472,423 | A * | 12/1995 | Gronauer ............... 604/102.01 |
| 5,531,664 | A | 7/1996 | Adachi et al. |
| 5,594,548 | A | 1/1997 | Kobayashi et al. |
| 5,633,675 | A | 5/1997 | Danna et al. |
| 5,658,238 | A * | 8/1997 | Suzuki et al. ............... 600/150 |
| 5,701,155 | A | 12/1997 | Wood et al. |
| 5,730,701 | A | 3/1998 | Furukawa et al. |
| 5,734,418 | A | 3/1998 | Danna |
| 5,743,731 | A | 4/1998 | Lares et al. |
| 5,754,220 | A * | 5/1998 | Smalser, Sr. ............... 348/84 |
| 5,754,313 | A | 5/1998 | Pelchy et al. |
| 5,801,825 | A | 9/1998 | Nutter et al. |
| 5,857,963 | A | 1/1999 | Pelchy et al. |
| 6,011,617 | A | 1/2000 | Naudet |
| 6,083,152 | A | 7/2000 | Strong |
| 6,097,848 | A | 8/2000 | Salvati |
| 6,111,599 | A * | 8/2000 | Nance et al. ............... 348/82 |
| 6,409,657 | B1 * | 6/2002 | Kawano ............... 600/157 |
| 6,468,201 | B1 | 10/2002 | Burdick |
| 6,483,535 | B1 | 11/2002 | Tamburrino et al. |
| 6,487,922 | B1 | 12/2002 | Bauer et al. |
| 6,494,739 | B1 | 12/2002 | Vivenzio et al. |
| 6,538,732 | B1 | 3/2003 | Drost et al. |
| 6,590,470 | B1 | 7/2003 | Burdick |
| 6,672,725 | B1 * | 1/2004 | VanOsdol et al. ............ 359/509 |
| 6,830,545 | B2 | 12/2004 | Bendall |
| 6,927,795 | B1 * | 8/2005 | Cazier et al. ............... 348/243 |
| 6,953,432 | B2 | 10/2005 | Schiefer |
| 7,134,993 | B2 | 11/2006 | Lia et al. |
| 7,170,677 | B1 | 1/2007 | Bendall et al. |
| 7,262,797 | B2 | 8/2007 | Weldum et al. |
| 2001/0013892 | A1 * | 8/2001 | Eversole et al. ............... 348/83 |
| 2003/0002036 | A1 * | 1/2003 | Haan et al. ............... 356/241.1 |
| 2003/0212308 | A1 | 11/2003 | Bendall |
| 2003/0233115 | A1 | 12/2003 | Eversull et al. |
| 2004/0183900 | A1 | 9/2004 | Karpen et al. |
| 2004/0199052 | A1 * | 10/2004 | Banik et al. ............... 600/142 |
| 2004/0215413 | A1 | 10/2004 | Weldum et al. |
| 2004/0233318 | A1 | 11/2004 | Schiefer |
| 2005/0050707 | A1 | 3/2005 | Scott et al. |
| 2005/0075538 | A1 * | 4/2005 | Banik et al. ............... 600/141 |
| 2005/0085842 | A1 * | 4/2005 | Eversull et al. ............ 606/191 |
| 2005/0129108 | A1 | 6/2005 | Bendall et al. |
| 2005/0154262 | A1 * | 7/2005 | Banik et al. ............... 600/179 |
| 2005/0162643 | A1 | 7/2005 | Karpen |
| 2005/0165275 | A1 | 7/2005 | Von Felten et al. |
| 2005/0168571 | A1 | 8/2005 | Lia et al. |
| 2005/0281520 | A1 | 12/2005 | Kehoskie et al. |
| 2006/0050983 | A1 | 3/2006 | Bendall et al. |
| 2006/0072903 | A1 | 4/2006 | Weldum et al. |
| 2007/0070340 | A1 | 3/2007 | Karpen |
| 2007/0091183 | A1 | 4/2007 | Bendall et al. |
| 2007/0156018 | A1 | 7/2007 | Krauter et al. |
| 2007/0156021 | A1 | 7/2007 | Morse et al. |
| 2007/0165306 | A1 | 7/2007 | Bendall et al. |
| 2007/0187574 | A1 | 8/2007 | Lia |
| 2007/0225931 | A1 | 9/2007 | Morse et al. |
| 2007/0226258 | A1 | 9/2007 | Lambdin et al. |

FOREIGN PATENT DOCUMENTS

| | | |
|---|---|---|
| DE | 2835331 A1 | 2/1980 |
| EP | 0907077 | 4/1999 |
| JP | 55026998 A1 | 2/1980 |
| JP | 01072722 | 3/1989 |
| JP | 64072722 | 3/1989 |
| JP | 02017024 | 1/1990 |
| JP | 02278219 | 11/1990 |
| JP | 05150171 | 6/1993 |
| JP | 11076154 | 3/1999 |
| JP | 2000046482 | 2/2000 |
| WO | WO 00/73762 | 12/2000 |
| WO | WO-03/090834 A2 | 11/2003 |
| WO | WO-03/090834 A3 | 11/2003 |
| WO | WO 2004/086957 A | 10/2004 |

OTHER PUBLICATIONS

Everest VIT, The Videoprobe XL Pro System Flying Probe User's Manual, 86 pages, Jun. 25, 2001.

Everest VIT, Flying XL Probe Complete With XL Pro Digital Feature Set, Product Specification Sheet, 2 pages, 2001.

Everest VIT Flying Videoprobe, Product Specification Sheet, 2 pages, 2003. This reference is believed to have been published more than one year prior to the critical date.

Bates, Stephen C., Pollack, Michael J., Gas Cooled Probe Protectors, Sep. 1999, SPIE vol. 3852, pp. 113-123.

Pollack, Michael, Taking Optical Probes Into Harsh Environments, May 2000—Measuring with Light, pp. 1-13.

* cited by examiner

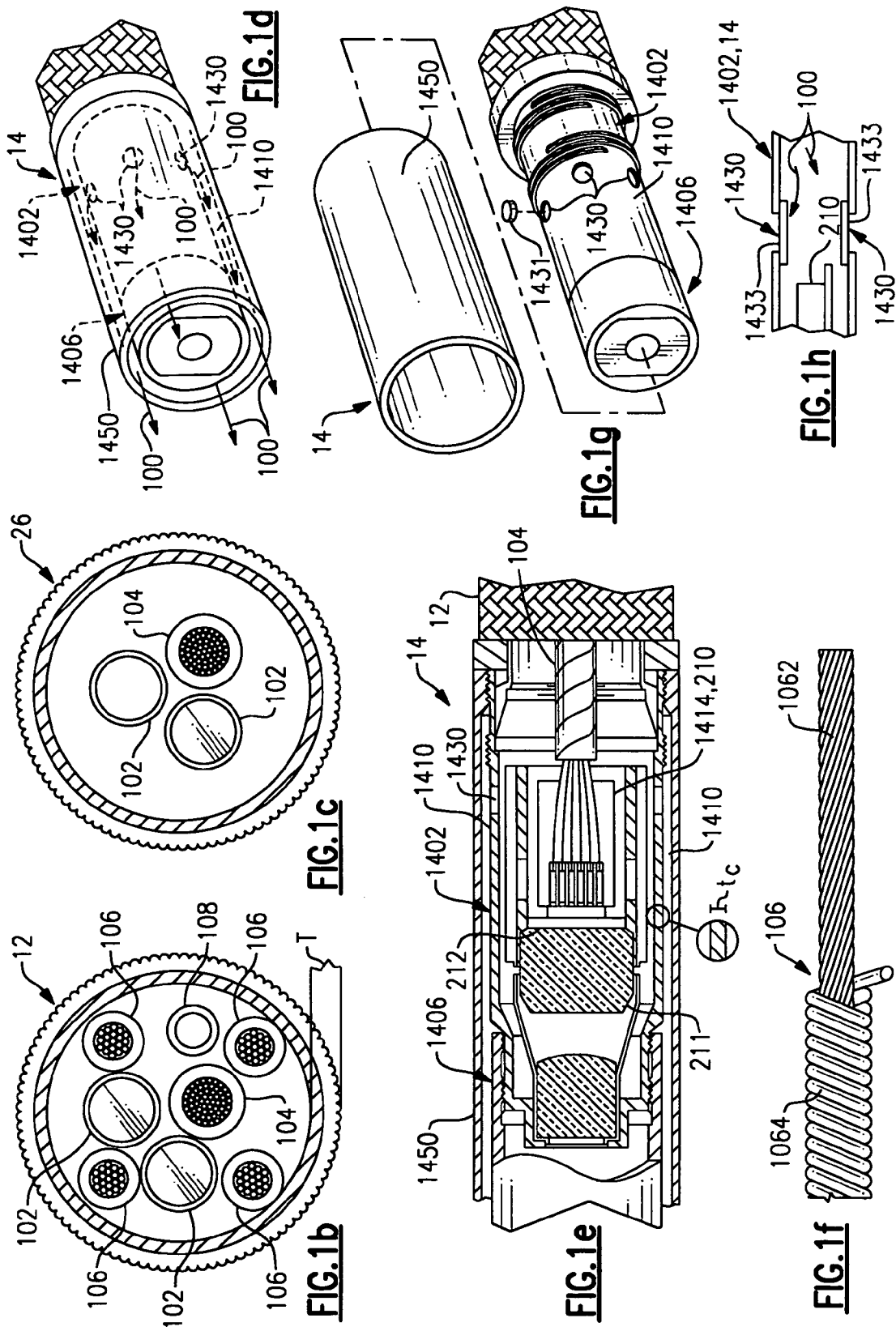

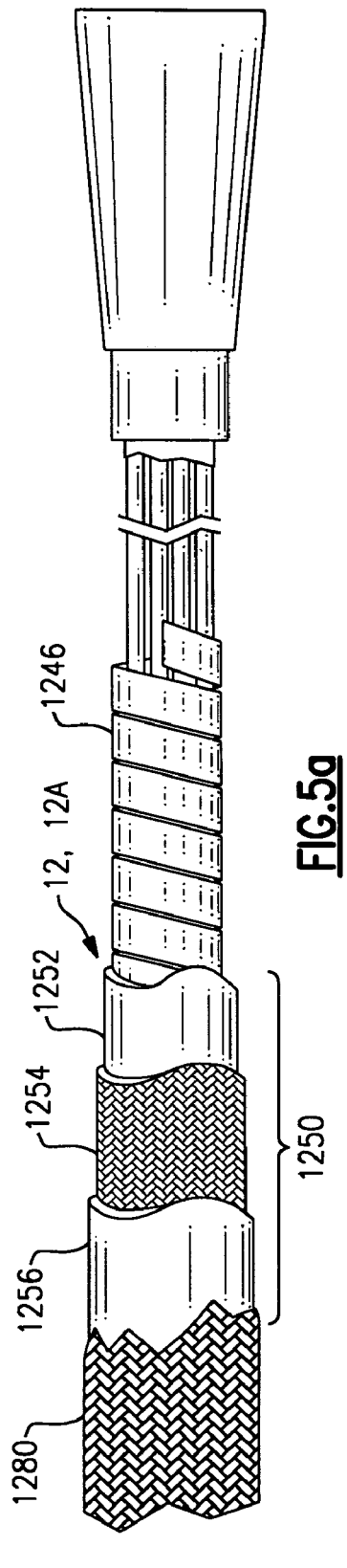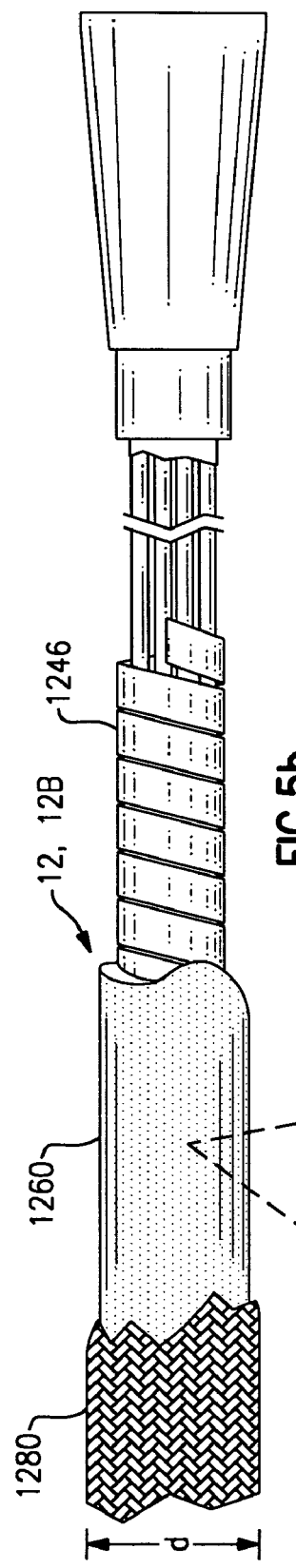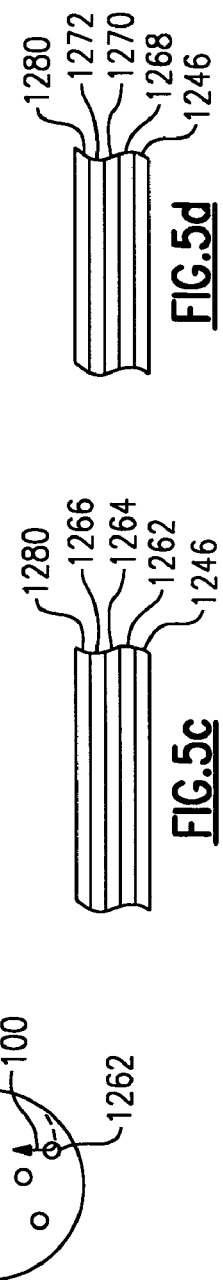
FIG.5a  FIG.5b  FIG.5c  FIG.5d

BORESCOPE COMPRISING FLUID SUPPLY SYSTEM

FIELD OF THE INVENTION

The invention relates to insertion tube remote viewing devices generally and specifically to insertion tube devices configured for use in specialized operating environments.

BACKGROUND OF THE PRIOR ART

A borescope is generally characterized as an elongated insertion tube which can be flexible with a viewing head at its distal or forward end. The borescope can also include a control housing at its proximal end for controlling or steering the forward end. Such a borescope has a bendable tube steering section or articulation section at the distal end adjacent to the viewing head. One or two pairs of control articulation cables extend through the articulation section and then through the remainder of the flexible insertion tube. These cables connect with a steering control in the control section. One or both pairs of these cables are differentially displaced to bend the articulation section. The viewing camera head assembly can thus be remotely oriented to facilitate the inspection of an object. Borescopes are intended for visual inspection of mechanical devices such as jet engines or turbines, where it would be difficult or impossible to examine the device's internal elements directly. If the borescope must be maneuvered into narrow tortuous passageways, the insertion tube must be flexible and must allow corresponding bending and steering. In addition, the pathway to the object can be quite long, and so it is often necessary that the borescope insertion tube be fifteen meters or more in length.

While several types of borescopes have been proposed, present borescopes have been observed to fail in specialized operating environments such as high temperature, high pressure, and liquid operating environments.

There is a need for a borescope adapted for use in specialized operating environments.

SUMMARY OF THE INVENTION

According to its major aspects and broadly stated, the invention is a borescope having a fluid supply system which is especially useful in cooling the borescope.

In one embodiment, a borescope camera head assembly is provided which has a metal canister and an insulating sleeve. Fluid exit holes or outlet openings are provided in the canister and the sleeve is configured so that fluid exiting the holes is directed by the sleeve to flow along the thermally conductive outer surface of the canister.

A fluid supply system of the invention can include a conduit which extends from an air inlet position at a hand piece of the borescope to a position within the borescope's insertion tube. The fluid delivery conduit can also extend from a fluid inlet position in a hand piece entirely through the insertion tube to the camera head assembly.

The insertion tube of the borescope can be configured to minimize temperature losses by way of temperature conduction along a surface of the insertion tube. In one example of the invention, the insertion tube includes a multilayer insulation layer assembly including a mesh fiberglass layer interposed between two sealing nonporous polytetrafluoroethylene layers. The inclusion of thermally insulative material in the insertion tube, such as a layer having the thermal conductivity of less than 0.50 BTU-in/(hr-ft/(hr-ft$^2$-F.°) reduces the entry of heat into the borescope through the insertion tube.

In another embodiment, the insertion tube is devoid of a fluid sealing layer and includes instead an insulating layer having micropores. The porous insulating layer allows fluid to escape through the walls of the insertion tube so that the insertion tube defines an insulating/cooling boundary layer, wherein the boundary layer reduces the entry of heat into the insertion tube. The porous insulating layer may have a thermal conductivity of less than 2.5 BTU-in/(hr-ft$^2$-F.°).

An insertion tube according to the invention can have a light reflective outer surface which reflects energy to further discourage the entering of heat into the insertion tube.

BRIEF DESCRIPTION OF THE DRAWINGS

For a further understanding of these and objects of the invention, reference will be made to the following detailed description of the invention which is to be read in connection with the accompanying drawings, wherein:

FIG. 1b is a cross section view of an insertion tube according to the invention;

FIG. 1c is a cross section view of an umbilical cord according to the invention;

FIG. 1d is a perspective view of a borescope camera head assembly according to the invention;

FIG. 1e is a section view of a camera head assembly according to the invention;

FIG. 1f is a side view of an articulation cable assembly according to the invention;

FIG. 1g is an exploded perspective view of a camera head assembly according to the invention;

FIG. 1h is a side view of a camera head assembly illustrating an embodiment of the invention including a bi-metallic valve.

FIGS. 5a-5b are side views of exemplary insertion tubes according to the invention;

FIGS. 5c-5d are cross section views of alternative insertion tubes according to the invention.

DETAILED DESCRIPTION OF THE INVENTION

Figure 1A:
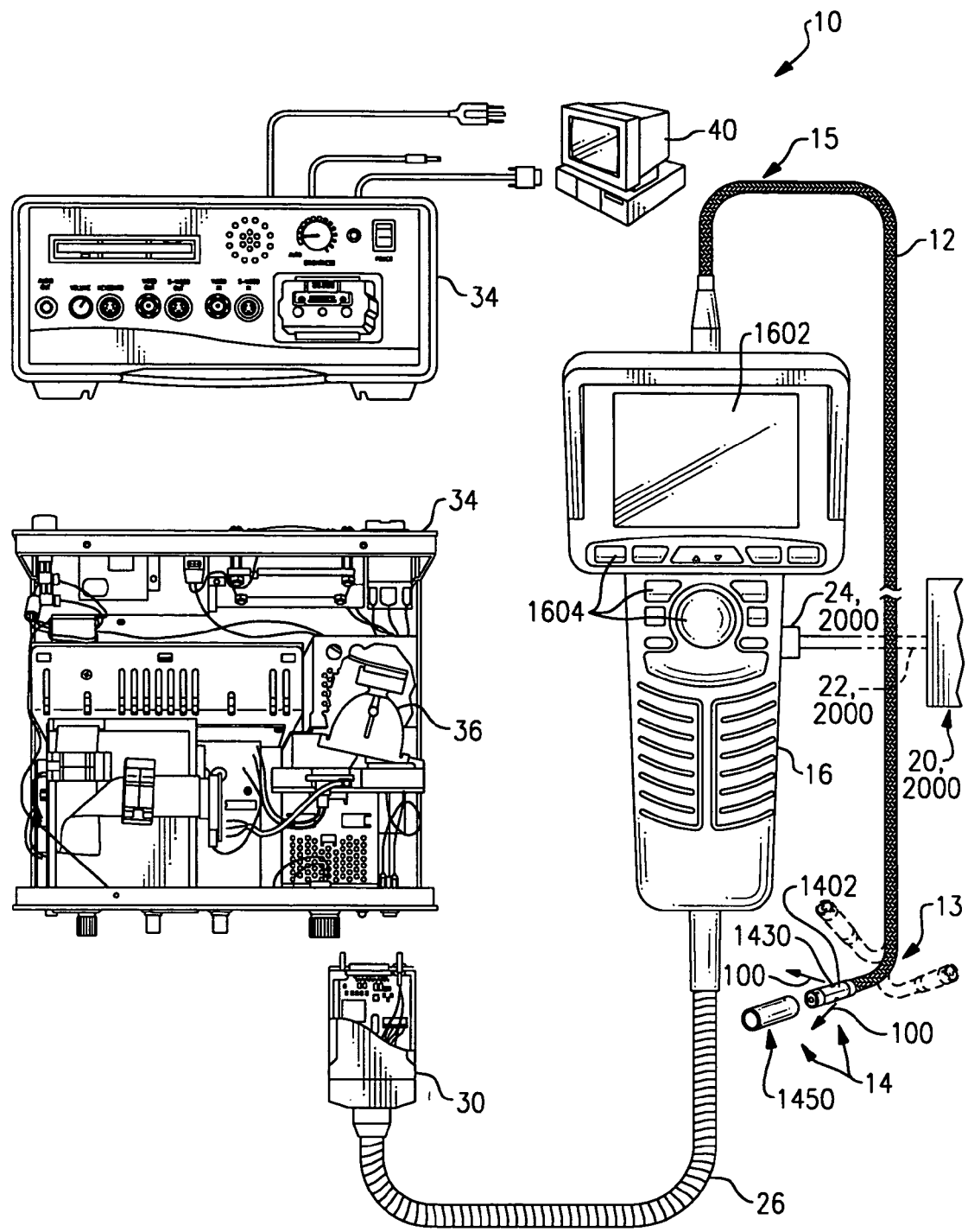
FIG. 1a is a physical layout diagram of a fluid delivering borescope of the invention.

A borescope 10, according to the invention, is shown in FIG. 1a. Borescope 10 includes flexible insertion tube 12, a camera head assembly 14, and hand piece 16. In accordance with the invention, fluid indicated by flow vectors 100 is forced down a length of insertion tube 12 and flows outwardly about head 1402 of camera head assembly 14 as indicated by fluid flow vectors 100 to cool electrical components of head assembly 14, improving reliability and consistency of performance of the electrical components. Fluid is conveniently supplied to borescope 10 by a fluid supply 20 which, through feed tube 22, is interfaced to connector 24 of hand piece 16. When attached, fluid supply 20, feed tube 22, and connector 24 may be considered part of borescope 10. As will be explained further herein, connector 24 may include a valve 1624 (FIG. 2) for use in regulating the flow of fluid from fluid supply 20. A fluid supply system 2000 of the borescope of FIG. 1a includes fluid supply 20, feed tube 22, and connector 24. Fluid delivered by the fluid supply system can include, for example, a mixture of nitrogen and oxygen (e.g., air), water, nitrogen, carbon dioxide, or inert gases such as helium or argon. The fluid delivered can also comprise a chlorofluorocarbon which changes state while traveling through the borescope 10. Borescope 10 may be part of the remote video inspection system described in U.S. patent application Ser. No. 10/768,761 filed Jan. 29, 2004 entitled, "Remote Video Inspection System" incorporated herein by reference.

Referring to aspects of borescope 10 in further detail, borescope 10 further includes umbilical cord 26, power plug 30 and light box 34. Disposed in light box 34 is a light source 36 which may be e.g., a 50-watt arc lamp, such as a type sold under SOLARC by Welch Allyn, Inc., Lighting Products Division, Skaneateles Falls, N.Y. Light box 34 may further carry an image processing circuit as will be described herein. Borescope 10 may further be in communication with a desktop monitor 40. Monitor 40 may be in communication with borescope 10 via several communication circuitries of light box 34.

Figure 4:
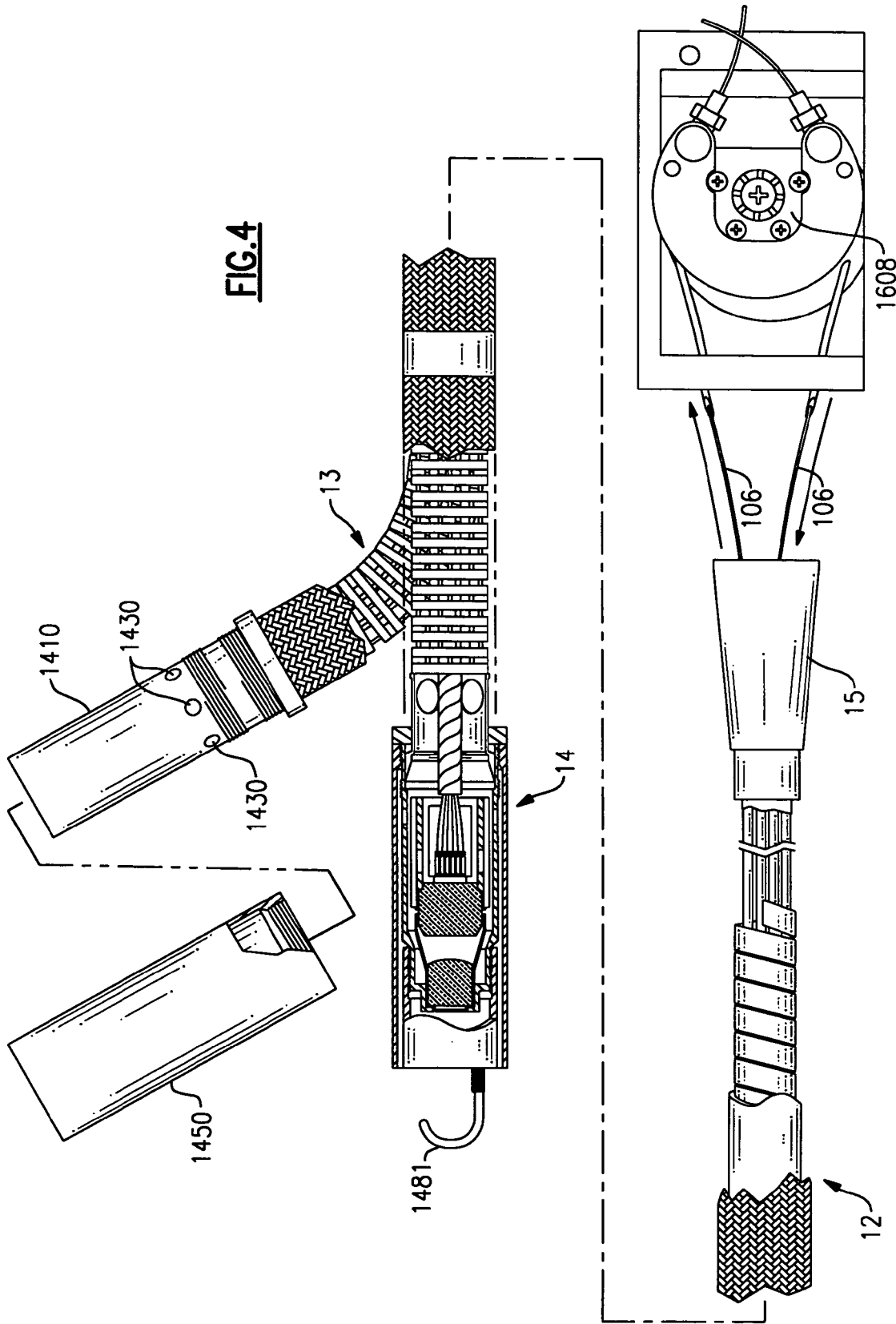
FIG. 4 is a side view of an exemplary insertion tube according to the invention.

Light source 36 of light box 34 directs light through umbilical cord 26, through hand piece 16, through insertion tube 12 and outwardly from camera head assembly 14. As seen by umbilical cord cross section view of FIG. 1c, umbilical cord 26 encases and supports fiber optic bundles 102. As seen by insertion tube cross section view FIG. 1b, insertion tube 12 also supports and encases fiber optic bundles 102. Referring to further aspects of umbilical cord 26, umbilical cord 26 further encases and supports wiring cable bundle 104. Part of the wires of wiring cable bundle 104 are branched off within hand piece 16 as is suggested by the electrical block diagram of FIG. 2 which will be discussed later herein. The remainder of the wires of bundle 104 extend through insertion tube 12 as is indicated by bundle 104 of insertion tube cross sectional view of FIG. 1b. Referring to insertion tube 12, insertion tube 12 as best seen in FIG. 1b carries fiber optic bundles 102, cable wiring bundle 104 (including flexible electrical conductors), articulation cable assemblies 106, and working channel 108. Articulation cable assemblies 106 provide for bending of insertion tube at distal end 13. As seen in the detail view of FIG. 1f, articulation cable assemblies 106 can be provided by a stranded cable 1062 encased by an outer spring conduit 1064. Working channel 108 allows manipulation of a tool (e.g., a hook 1481 as seen in FIG. 4, a brush, or a magnet) extending from camera head assembly 14. While borescope 10 having the insertion tube embodiment of FIG. 1b includes fiber optic bundles 102, it will be understood that the illumination system having light source 36 and bundles 102 can be replaced or supplemented by an illumination system comprising light sources such as a plurality of LEDs incorporated in head 14. LEDs in head assembly 14, like image sensor 212 (FIG. 1e) and image signal conditioning circuit 210 (FIG. 2), may be powered by power delivery conductors of bundle 104.

Figure 2:
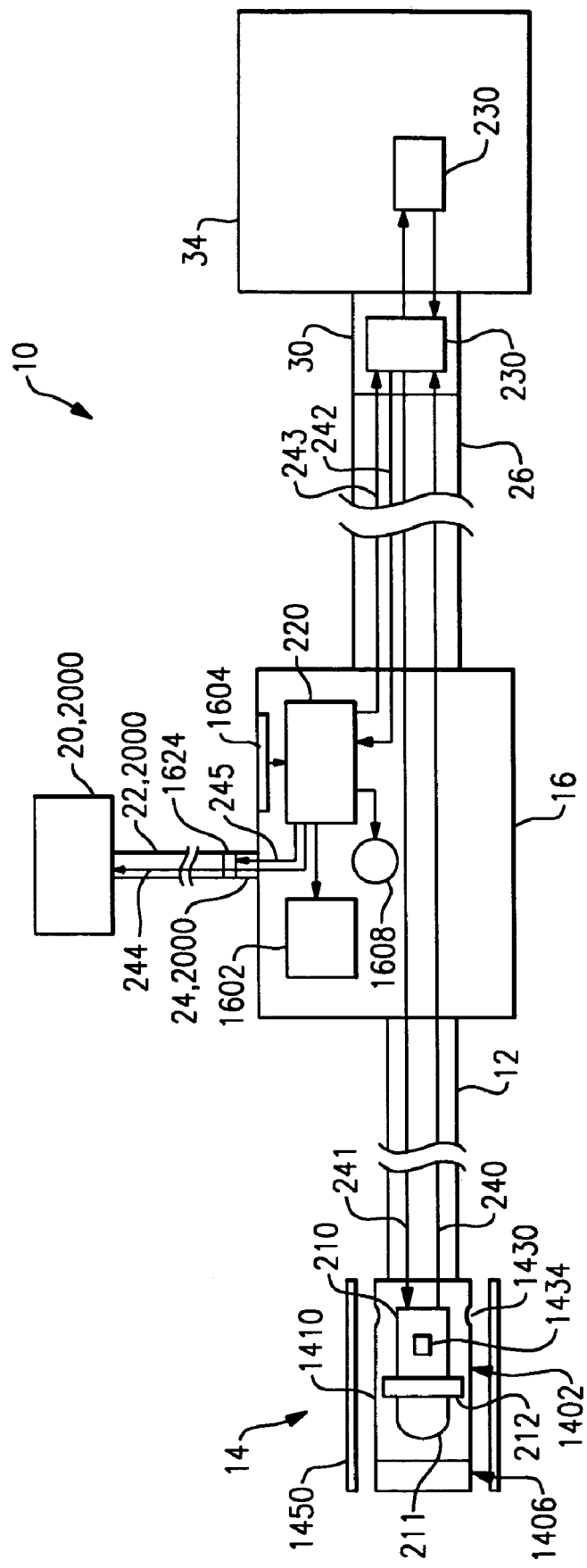
FIG. 2 is a block electrical layout diagram of a borescope electrical and control system according to the invention.

A functional block electrical layout diagram is shown in FIG. 2. Various electrical circuits are distributed throughout borescope 10. In one typical layout scheme, borescope 10 includes an image signal conditioning circuit 210, a hand piece control circuit 220 and an image processing circuit 230. Image signal conditioning circuit 210 receives image signal clocking and controls signals from image processing circuit 230 for control of image sensor 212, and conditions analog image signals generated by image sensor 212 so that the signals can be delivered to image processing circuit 230. Image sensor 212 is typically a 2D color solid-state image sensor. Image processing circuit 230 may be partially distributed in power plug 30 and partially distributed in light box 34. Among other functions, image processing circuit 230 receives analog image signals as transmitted by image signal conditioning circuit 210, converts such signals into digital form utilizing an analog-to-digital converter and buffers frames of image data so that frames of image data can be subjected to various processing. The processing which may be performed by image processing circuit 230 can include such processing as single frame storage, measurement determination, and object recognition. Image processing circuit 230 can also perform such functions as overlaying of menu interface selection screens on displayed images, and transmitting output video signals to various displays such as hand piece display 1602 and monitor display 40. In addition to housing image processing circuit 230, power plug 30 and light box 34 also carry various electrical circuitries for delivering electrical power to various components of borescope 10. Electrical communication between the various circuits is provided by signal lines 240, 241, 242, and 243, each of which represents one or more electrical conductors. Signal lines 244, 245 to be discussed further herein also represent one or more electrical conductors.

Hand piece control circuit 220 (which may also be termed a video probe control circuit), among other functions, receives video signals from image processing circuit 230, and displays such signals on display 1602 of hand piece 16, receives user input and commands input via hand piece controls 1604 and interprets such inputs to perform various operations. One important function of hand piece control circuit 220 is to receive insertion tube control inputs. Hand piece control circuit 220 interprets user inputs to develop control signals for controlling control servomotor 1608 which moves articulation cables 1062 so that a distal end 13 of insertion tube 12 is moved into a desired orientation. Control circuit 220 may also adjust control signals input into fluid supply 20 and or connector 24 as will be explained further herein.

Image processing circuit 230 and hand piece processing circuit 220 are typically microprocessor based; that is, they are conveniently established utilizing one or a plurality of readily available programmable off-the-shelf microprocessor integrated circuit (IC) chips. Microprocessor IC chips often have on-board volatile and nonvolatile memory structures and are typically implanted in communication with external volatile and nonvolatile memory devices. Exemplary integrated circuit parts for use in realizing circuit elements of FIG. 2 are listed in Table 1.

TABLE 1

| | |
|---|---|
| Image Sensor 212 | Sony ICX238EKU-E (NTSC) |
| | Sony ICX239EKU-E (PAL) |
| Image Processing Circuit 230 | Rockwell Decoder BT829 |
| | Rockwell Encoder BT866 |
| | Xilinx FPGA Controller XC4020 |
| Control Circuit 220 | Hitachi HD64F3642AH |

Figure 3A:
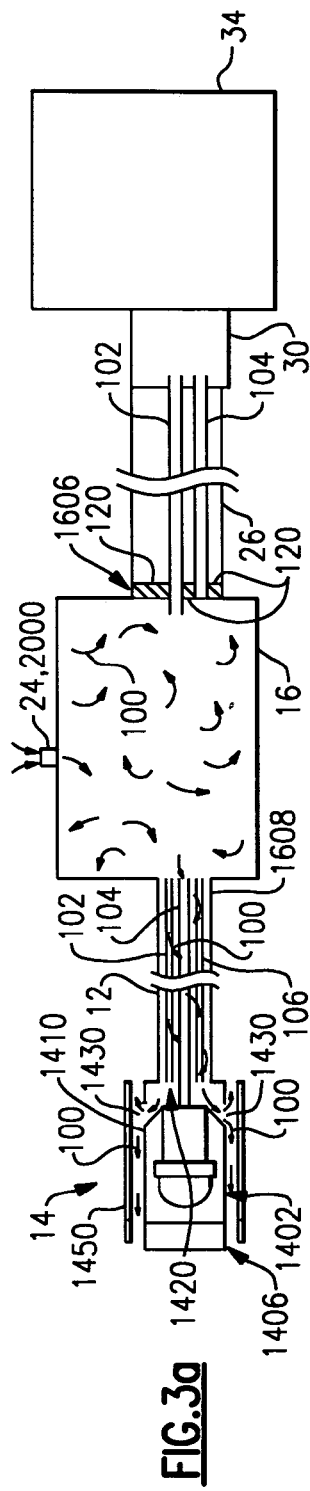
FIGS. 3a, 3b, and 3c are functional schematic diagrams illustrating various fluid supply systems of the invention.
Figure 3B:
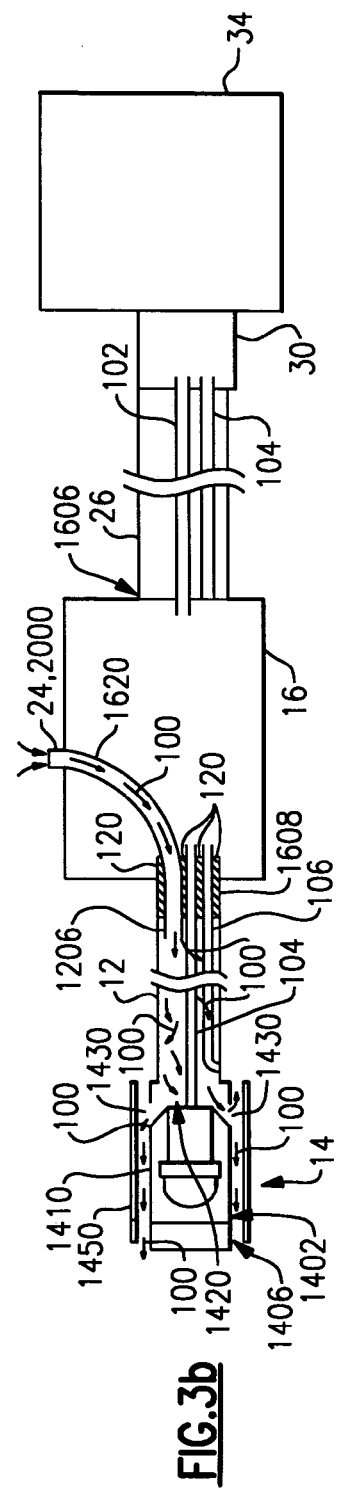
Figure 3C:
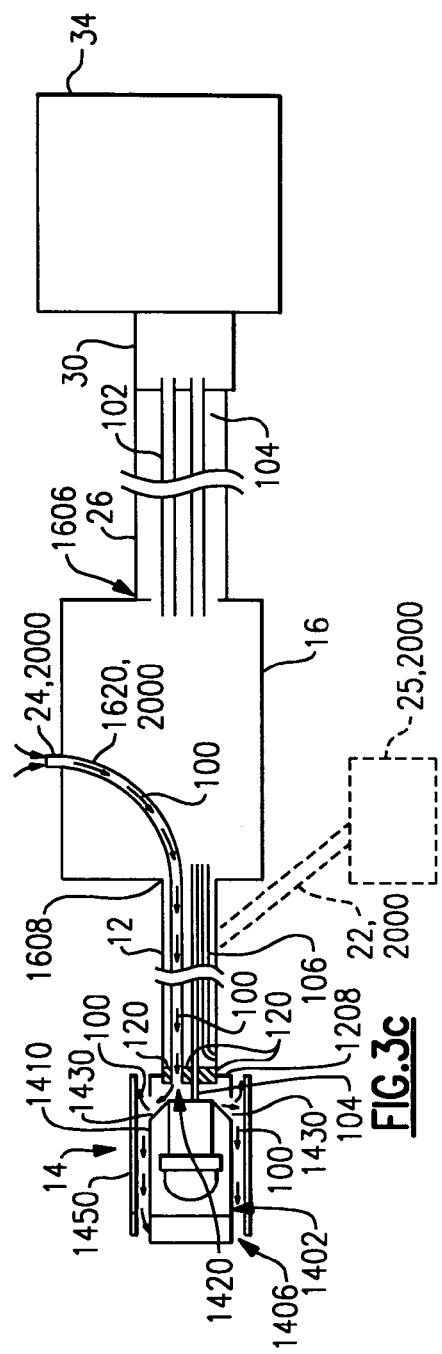

FIGS. 1d and 1e show detailed views of a camera head assembly 14 which is cooled by the present invention. Camera head assembly 14 includes head 1402 and tip 1406. Tip 1406, normally of detachable construction includes various lenses which determine a field of view (e.g., straight view, right angle view, narrow right angle, wide right angle, etc.) while head 1402 carries camera components. More specifically, head 1402 includes metal canister 1410 which encapsulates lens 211, image sensor 212 and IC chip 1414 in which the elements of the aforementioned image signal conditioning circuit 210 are incorporated. The inventors observed that the performance of image sensor 212 and circuit 210 degrades significantly when those components are subjected to higher temperatures such as temperatures above 185° (degrees) Fahrenheit. In the present invention, camera head assembly 14 is configured so that sensitive electrical components within the head 1402 can be cooled. In accordance with the present invention, as best seen in FIGS. 3a-3c, head assembly 14 has fluid inlet opening 1420 and fluid outlet openings 1430. In the embodiment of FIG. 3a, a fluid inlet opening 1420 is delimited by the interior circumference of a wall insertion tube 12 which will be explained is of a stacked construction. Fluid outlet openings 1430 of head assembly 14 are formed in the walls of canister 1410. To the end that cooling fluid flowing out of outlet opening 1430 is directed along the outer surface of canister 1410, a sleeve 1450 is provided which is fitted about canister 1410. Sleeve 1450 operates to limit the flow of outlet cooling fluid so that the cooling fluid indicated by vectors 100 has a maximal cooling affect on canister 1410 and, therefore, the electrical components therein. Canister 1410 is heat-conductive so that the interior wall temperature of canister 1410 is substantially equal to that of the cooled outer walls of canister 1410. In one example, canister 1410 comprises stainless steel and comprises a wall thickness, $T_c$, of from about 0.005 inches to about 0.010 inches. According to the invention, fluid indicated by vectors fluid flow 100 is also forced in close proximity with electrical components as is indicated by fluid flow vectors 100 as shown in FIGS. 1a, 1d, 1h, 3a, 3b, and 3c.

In one variation of the invention, head 1402 incorporates a thermal sensing element for control of application of fluid about canister 1410. For example, in one embodiment passive temperature responsive bimetallic valves 1433 as shown in FIG. 1h may be disposed at the respective openings 1430 of canister 1410. Such valves are in a normally closed position and automatically open when a temperature exceeds a predetermined level. In certain bimetallic valves, the amount of opening of the valve varies depending on sensed temperature.

In another embodiment, a thermistor 1434 in FIG. 2 is disposed in or, alternatively, in proximity with image signal condition circuit 210 of head 1402. A temperature indicating signal produced by thermistor 1434 may be in electrical communication with control circuit 220. When the specific integration of FIG. 2 is employed, the temperature information of thermistor 1434 may be sent to image processing circuit 230 via line 240, which routes the information to control circuit 220 via line 242. In response to the temperature indicating signal received from thermistor 1434, control circuit 220 adjusts a fluid control signal input to fluid supply 20 via signal line 244 to adjust the delivery of fluid into head 1402 depending on the temperature of head 1402. A fluid control signal input into fluid supply 20 may open a valve (not shown) of fluid supply 20 to increase a pressure of fluid within insertion tube 12 and head assembly 14 when a temperature sensed by thermistor 1434 exceeds a predetermined value. The control signal input into fluid supply 20 may also adjust a temperature of fluid supplied by fluid supply 20. In the alternative or in addition, control circuit 220 may send to connector 24 via signal line 245 a fluid control signal which controls the opening of connector valve 1624 in response to the temperature indicating signal received from thermistor 1434.

Rather than incorporating a dedicated thermistor 1434 for sensing temperature of head 1402 and there from regulating fluid characteristics, borescope 10 may sense the temperature of head 1402 by processing of image signals generated by image sensor 212. Borescope can be configured so that image signals output by solid state image sensor 212 include temperature indicating signals. More specifically, the inventors noted that specific noise characteristics are observed in electrical signals generated by image sensor 212 above certain temperatures. For example, above a certain temperature that depends on system characteristics (e.g., type of image sensor, electrical packaging) unwanted vertical lines appear in a captured frame of image data. Above another certain temperature, an unwanted color shift is exhibited in a captured frame of image data. Accordingly, in a highly useful embodiment of the invention, image processing circuit 230 monitors frames of captured image data for noise characteristics indicative of a temperature in head 1402 exceeding a predetermined level. In response to image processing circuit 230 processing the image signals from image sensor 212 and determining that a temperature of head 1402 has exceeded a certain level, image processing circuit 230 by an appropriate communication to control circuit 220 may adjust fluid control signals transmitted in lines 244 and/or 245 to fluid supply 20 and/or valve 1624. It is understood that control circuit 220 may regulate fluid flow and temperature in the embodiment where temperature is sensed by processing of image data in the same manner that control circuit 220 regulates fluid flow and temperature when temperature is sensed by monitoring a temperature indicating signal from thermistor 1434. That is, regardless of the apparatus used in the sensing of temperature, control circuit 220 may transmit a control signal to fluid supply system 2000 which increases cooling fluid pressure (and, therefore, flow volume) when the temperature of head 1402 requires lowering. Control circuit 220 may also transmit a fluid control signal to fluid supply system 2000 which lowers a temperature of fluid supplied by fluid supply 20 when the temperature of head 1402 requires lowering.

In another aspect, check valves 1431 are disposed at openings 1430 as is indicated by FIG. 1g. Check valves 1431 allow fluid to escape canister 1410 when insertion tube 12 and/or head 14 are pressurized, but close to seal canister 1410 when tube 12 and/or head 14 are not pressurized.

Referring to FIGS. 3a-3c, several alternative schemes for forcing fluid through borescope 10 are possible. In the embodiment of FIG. 3a, the entire hand piece 16 is substantially pressure sealed. Forms of the term "seal" herein encompass perfect seals (no fluid escape) and structures which, though deviating from a perfect seal, are intended to allow a minimal amount of fluid escape. The joints, seams, and screw holes of hand piece 16 are pressure sealed. The interface 1606 between umbilical cord 26 and hand piece 16 is sealed as is indicated by sealant 120. When fluid is input into a hand piece 16, the fluid, as is indicated by arrows 100, is forced outward through insertion tube 12 and eventually outward about camera head assembly 14 in the manner described with reference to FIGS. 1d and 1e. Connector 24 defines a fluid input point in the embodiments of FIG. 3a, 3b, and 3c.

In the embodiment of FIG. 3b, a conduit 1620 extends from connector 24 to a position 1206 within insertion tube 12 and terminates within insertion tube (at prominal end thereof) in the embodiment shown. Interface 1608 between insertion tube 12 and hand piece 16 is sealed as is indicated by sealant 120. In the embodiment of FIG. 3c, a conduit 1620 extends from connector 24 at hand piece 16 all the way though insertion tube 12 and terminates at camera head assembly 14. In the embodiment of FIG. 3c, fluid entering connector 24 is forced through conduit 1620 to head assembly 14 where the cooling fluid flows in the manner described with reference to FIGS. 1d and 1e. The interface 1208 between insertion tube 12 and camera head assembly 14 may be sealed to further encourage flow of coolant about head assembly 14 as is indicated by sealant 120 of FIG. 3c. In yet another embodiment, feed tube 22 is directly interfaced to insertion tube 12 as is shown by dashes in feed tube 22 and fluid supply 25 of FIG. 3c.

Sealant 120, which is made to conform about bundles 102, bundle 104, working channel 108, and cable assemblies 106 may be provided, for example, by epoxy sealant, or high temperature RTV. Bundles 102 are deleted from the view of FIGS. 3b and 3c for simplicity purposes. Epoxy sealants which may be used may be e.g., type EP42HT, EP21TDCHT, EP42a+TND-2TG epoxies. The above epoxies, which all have operating temperatures of 350° (degrees) Fahrenheit or higher, are available from Masterbond, Inc.

Further aspects of the invention relating to the structure of insertion tube 12 are described with reference to FIGS. 4-5d. As seen in FIGS. 4-5d, an insertion tube 12, according to the invention, is generally of a multi layer stacked up construction. In a typical prior art insertion tube, an insertion tube comprises polyurethane. The inventors discovered that at higher temperatures, polyurethane melts, damaging or destroying insertion tube 12. The melting point of the polyurethane is typically in the range of 400° (degrees) Fahrenheit. In accordance with the present invention, insertion tube 12 is entirely devoid of polyurethane and entirely devoid of materials having a "low" melting point, e.g., a melting point of less than 400° (degrees) Fahrenheit. That is in one embodiment, layers 1246, 1252, 1254, 1256, 1270 (FIG. 5a) as well as "lines" 102, 104, 106, 108 (FIG. 1b) all have a melting point of at least 400° (degrees) Fahrenheit so that borescope 10 is operational in high temperature conditions.

The inventors also found that the cooling of head 14 of borescope 10 becomes more challenging as insertion tube 12 becomes longer. Heat enters borescope 10 through insertion tube 12. The amount of heat that enters borescope 10 increases as insertion tube is made longer. In accordance with the invention, in another aspect as will be described herein, insertion tube 12 may comprise at least one layer that has a thermal conductivity of less than about 0.50 BTU-in/(hr-ft$^2$-F.°) e.g., fiberglass, which is available in a form having thermal conductivity of 0.27 BTU-in/(hr-ft$^2$-F.°). In another embodiment, insertion tube 12 has at least one thermally insulating layer having a thermal conductivity of less than 2.5 BTU-in/(hr-ft$^2$-F.°).

In the example of FIG. 5a, insertion tube 12 includes an insulation layer assembly 1250. Insulation layer assembly 1250, in the embodiment of FIG. 5a, comprises three layers. First layer 1252 is a nonporous seal layer comprising polytetrafluoroethylene. Second layer 1254 is an insulating layer comprising mesh (porous) fiberglass. Second layer 1254 is substantially thermally insulating. Third layer 1256 is another nonporous polytetrafluoroethylene seal layer. A three layer system can limit conduction through the interior and exterior layers by creating a thermal barrier. Referring to other layers of insertion tube 12, layer 1246 is a monocoil. Layer 1246 increases the crush resistance of insertion tube 12. Layer 1280 is a mesh tungsten layer. Tungsten layer 1280 increases the abrasion resistance and torsional stiffness of insertion tube 12.

The multi-layer insulation layer assembly may be used in combination with any of the fluid input systems as shown in FIGS. 3a-3c.

Another embodiment of an insertion tube in accordance with the invention is shown in FIG. 5b. In the embodiment of FIG. 5b, the multilayer insulation layer assembly of FIG. 5b is replaced with a single layer insulation assembly devoid of a sealing layer. In the embodiment of FIG. 5b, insulating layer 1260 comprises a porous, non-sealing tube 1260. Layer 1260 may have the structure as shown in FIG. 5b in which micropores 1262 are dispersed throughout. Micropores 1262 may have diameters ranging from about 10 microns to about 100 microns. Micropores 1262 may be nonuniformly sized, and nonuniformly spaced. Micropores 1262 may also be randomly sized and randomly spaced. Micropores 1262 allow cooling fluid indicated by vectors 100 to escape there through. By the action of fluid escaping from micropores 1262, an insulating/cooling boundary layer is formed along the outside surface of insertion tube 12. The insulation/cooling boundary reduces heat entry into insertion tube 12 by way of convection. The insertion tube 12 of FIG. 5b may be used in combination with any of the embodiments of FIGS. 3a, 3b, and 3c.

In a variation of the invention, micropores 1262 are nonuniformly formed throughout the length of insertion tube 12 according to a specific dispersion pattern. In one example, insertion tube 12 is configured so that there is a progressively higher density of micropores 1262 from proximal end 15 of insertion tube 12 to distal end 13 of insertion tube 12 (FIG. 4). If insertion tube 12 is made to have a progressively higher density of micropores 1262 from proximal end 15 to distal end 13, and the density progression is appropriately designed, fluid escapes from insertion tube 12 uniformly throughout the length of insertion tube 12. Micropore "density" herein refers to the total area consumed by micropores 1262 per unit length. Therefore, a progressively higher density of micropores 1262 can be provided by increasing the number of micropores and/or increasing the average size of the micropores along the length of insertion tube 12. Various examples of the invention are described with reference to Tables 2A-2D.

TABLE 2A

| Layer | Material | Trade Name | Thermal Conductivity | Maximum Operating Temperature | Thickness |
|---|---|---|---|---|---|
| Monocoil 1246 | Stainless Steel | | 138.8 BTU-in/(hr-ft²-F. °) | 2550° F. | 0.010 in. |
| Layer 1252 | Nonporous Polytetrafluoroethylene | TEFLON | 2.08 BTU-in/(hr-ft²-F. °) | 500° F. | 0.010 in. |
| Layer 1254 | Porous Fiberglass | TEFLON | 0.27 BTU-in/(hr-ft²-F. °) | 1200° F. | 0.012 in. |
| Layer 1256 | Nonporous Polytetrafluoroethylene | TEFLON | 2.08 BTU-in/(hr-ft²-F. °) | 500° F. | 0.010 in. |
| Layer 1280 | Tungsten braid | | 1130 BTU-in/(hr-ft²-F. °) | 6100° F. | 0.006 in. |

The structure summarized in Table 2A is shown in FIG. 5a. The porous fiberglass layer provides a thermal barrier and limits the entry of heat into insertion tube by way of thermal conduction. The polytetrafluoroethylene layers seal the insertion tube, and limit the entry of fluid through the walls of insertion tube 12.

TABLE 2B

| Layer | Material | Trade Name | Thermal Conductivity | Maximum Operating Temperature | Thickness |
|---|---|---|---|---|---|
| Monocoil 1246 | Stainless Steel | | 138.8 BTU-in/(hr-ft²-F. °) | 2550° F. | 0.010 in. |
| Layer 1260 | Porous Polytetrafluoroethylene | SILKORE | | Excellent high temp integrity | 0.015 in. |
| Layer 1280 | Tungsten braid | | 1130 BTU-in/(hr-ft²-F. °) | 6100° F. | 0.006 in. |

The structure summarized in Table 2B is shown in FIG. 5b. Pressurized fluid is allowed to escape from the walls insertion tube 12 to provide an insulation/cooling boundary.

TABLE 2C

| Layer | Material | Trade Name | Thermal Conductivity | Maximum Operating Temperature | Thickness |
|---|---|---|---|---|---|
| Monocoil 1246 | Stainless Steel | | 138.8 BTU-in/(hr-ft²-F. °) | 2550° F. | 0.010 in. |
| Layer 1262 | Nonporous Meta-Phenelyneisophthalamide layers | NOMEX | 0.715 BTU-in/(hr-ft²-F. °) | 428° F. | 0.015 in. |
| Layer 1264 | Porous Fiberglass | | 0.27 BTU-in/(hr-ft²-F. °) | 1200° F. | 0.012 in. |
| Layer 1266 | Nonporous Meta-Phenelyneisophthalamide | NOMEX | 0.715 BTU-in/(hr-ft²-F. °) | 428° F. | 0.015 in. |
| Layer 1280 | Tungsten braid | | 1130 BTU-in/(hr-ft²-F. °) | 6100° F. | 0.006 in. |

The structure summarized in Table 2C is shown in FIG. 5c. The structure of FIG. 5c is similar to the structure of FIG. 5a, with the polytetrafluoroethylene layers replaced with meta-phenelyneisophthalamide layers.

TABLE 2D

| Layer | Material | Trade Name | Thermal Conductivity | Maximum Operating Temperature | Thickness |
|---|---|---|---|---|---|
| Monocoil 1246 | Stainless Steel | | 138.8 BTU-in/(hr-ft²-F. °) | 2550° F. | 0.010 in. |
| Layer 1268 | Nonporous Poly-paraphenylene terephthalamide | KEVLAR | 0.277 BTU-in/(hr-ft²-F. °) | 797° F. | 0.015 in. |
| Layer 1270 | Porous Fiberglass | | 0.27 BTU-in/(hr-ft²-F. °) | 1200° F. | 0.012 in. |
| Layer 1272 | Nonporous Poly-paraphenylene terephthalamide | KEVLAR | 0.277 BTU-in/(hr-ft²-F. °) | 797° F. | 0.015 in. |
| Layer 1280 | Tungsten braid | | 1130 BTU-in/(hr-ft²-F. °) | 6100° F. | 0.006 in. |

The structure summarized in Table 2D is shown in FIG. 5d. The structure of FIG. 5d is similar to the structure of FIG. 5a with the polytetrafluoroethylene layers replaced with poly-paraphenylene terephthalamide.

Referring to further aspects of insertion tube 12, in one embodiment insertion tube 12 may have an outer diameter "d," at (FIGS. 5a, 5b) from about 4 mm to about 12 mm. Tube 12 (FIG. 5a) may have a total thickness (the thickness of stacked up layers 1246, 1280 and intermediate layers) from about 1 mm to about 5 mm in one example.

Insertion tube 12 can also have a construction in accordance with one or more of the embodiments described in U.S. patent application Ser. No. 10/763,131 filed Jan. 22, 2004 and entitled, "Inspection Device Insertion Tube" incorporated herein by reference.

Referring to aspects of fluid supply 20, fluid supply 20 can take on a variety of forms. Fluid supply 20 can be provided, for example, by an air compressor, or an air cylinder. Fluid that is supplied by fluid supply 20 may be, for example, a mixture of nitrogen and oxygen (e.g., air), water, nitrogen, carbon dioxide, or inert gases such as helium or argon. Fluid supply 20 can be a standardly known industrial low pressure compressed air supply. Fluid supply 20 can also be a stand alone commercial compressor (electric or gas) as are known to skilled artisans.

While the present invention has been particularly shown and described with reference to the preferred mode as illustrated in the drawing, it will be understood by one skilled in the art that various changes in detail may be affected therein without departing from the spirit and scope of the invention as defined by the claims.

We claim:

1. An insertion tube remote viewing device comprising:
an insertion tube having a wall and carrying at least one of an articulation cable, a fiber bundle, and a wire bundle, wherein said wall is of a multilayer stacked up construction; a fluid supply system; and
a camera head assembly disposed at a distal end of said insertion tube, wherein said multilayer wall of said insertion tube is devoid of material having a melting temperature lower than about 400° (degrees) Fahrenheit;
wherein said multilayer wall includes a layer selected from the group consisting of nonporous polytetrafluoroethylene, meta-phenelyneisophthalamide, and poly-paraphenylene terephthalamide, and wherein said multilayer wall further includes a layer of porous fiberglass having a thermal conductivity of less than 0.50 BTU-in/(hr-ft²-F.°); and
wherein said insertion tube remote viewing device is configured to receive fluid from said fluid supply system.

2. The insertion tube remote viewing device of claim 1, wherein said multilayer wall includes a layer of meta-phenelyneisophthalamide.

3. The insertion tube remote viewing device of claim 1, wherein said multilayer wall includes a layer of nonporous polytetrafluoroethylene.

4. The insertion tube remote viewing device of claim 1, wherein said layer selected from the group consisting of nonporous polytetrafluoroethylene, meta-phenelyneisophthalamide, and poly-paraphenylene terephthalamide is disposed adjacent to said layer of porous fiberglass having a thermal conductivity of less than 0.50 BTU-in/(hr-ft²-F.°).

5. An insertion tube remote viewing device comprising:
an insertion tube having a wall and carrying at least one of an articulation cable, a fiber bundle, and a wire bundle, wherein said wall is of a multilayer stacked up construction;
a camera head assembly disposed at a distal end of said insertion tube;
a solid state image sensor disposed in said camera head assembly;
an image processing circuit that processes image signals of said solid state image sensor, wherein said multilayer insertion tube includes at least one porous fiberglass layer having a thermal conductivity of less than 0.50 BTU-in/(hr-ft²-F.°);
wherein said multilayer insertion tube further includes a nonporous layer of material layered adjacent to said porous layer; and
wherein said insertion tube remote viewing device is configured to receive fluid from a fluid supply system.

6. The insertion tube remote viewing device of claim 5, wherein said layer of porous fiberglass is disposed internally relative to said nonporous layer.

7. The insertion tube remote viewing device of claim 5, wherein said nonporous material layer is selected from the group consisting of polytetrafluoroethylene, meta-phenelyneisophthalamide, and poly-paraphenylene terephthalamide.

8. An insertion tube remote viewing device comprising:
an insertion tube having a wall and carrying at least one of an articulation cable, a fiber bundle, and an electrical conductor, wherein said wall is of a multilayer stacked construction;
a fluid supply system; and
a camera head assembly disposed at a distal end of said insertion tube;

wherein said multilayer wall is devoid of a sealing layer and includes a microporous layer having micropores formed therein, and wherein fluid delivered by said fluid supply system escapes from said micropores of said microporous layer; and wherein said multilayer insertion tube wall further includes a non-sealing abrasion resistant wire braid layer disposed about said microporous layer.

9. The insertion tube remote viewing device of claim 8, wherein said multilayer insertion tube wall further includes a non-sealing monocoil, wherein said microporous layer is disposed about said monocoil.

10. The insertion tube remote viewing device of claim 8, wherein said microporous layer has a melting point of at least 500° (degrees) Fahrenheit.

11. The insertion tube remote viewing device of claim 8, wherein said microporous layer consists of polytetrafluoroethylene.

12. The insertion tube remote viewing device of claim 8, wherein said micropores are formed with progressively higher density throughout a length of said insertion tube from a proximal end of said insertion tube to a distal end thereof.

13. The insertion tube remote viewing device of claim 8, wherein said camera head assembly has formed thereon a plurality of fluid outlet openings, and wherein fluid delivered by said fluid supply system escapes said camera head assembly through said fluid outlet openings.

14. The insertion tube remote viewing device of claim 8, wherein said insertion tube remote viewing device further includes a thermal sensor disposed to sense a temperature of said camera head assembly and an image sensor disposed in said camera head assembly, wherein said fluid supply system is responsive to said temperature, and wherein said thermal sensor is provided by one of a dedicated temperature sensor or said image sensor.

15. An insertion tube remote viewing device comprising:
an insertion tube having a wall and carrying at least one of an articulation cable, a fiber bundle, and an electrical conductor, wherein said wall is of a multilayer stacked construction;
a fluid supply system; and
a camera head assembly disposed at a distal end of said insertion tube;
wherein said multilayer wall is devoid of a sealing layer and includes a microporous layer having micropores formed therein, and wherein fluid delivered by said fluid supply system escapes from said micropores of said microporous layer; and
wherein said micropores are formed with progressively higher density throughout a length of said insertion tube from a proximal end of said insertion tube to a distal end thereof.

16. The insertion tube remote viewing device of claim 15, wherein said multilayer insertion tube wall further includes a non-sealing abrasion resistant wire braid layer disposed about said microporous layer.

17. The insertion tube remote viewing device of 15, wherein said multilayer insertion tube wall further includes a non-sealing monocoil, wherein said microporous layer is disposed about said monocoil.

18. The insertion tube remote viewing device of claim 15, wherein said microporous layer has a melting point of at least 500° (degrees) Fahrenheit.

19. The insertion tube remote viewing device of claim 15, wherein said microporous layer consists of polytetrafluoroethylene.

20. The insertion tube remote viewing device of claim 15, wherein said camera head assembly has formed thereon a plurality of fluid outlet openings, and wherein fluid delivered by said fluid supply system escapes said camera head assembly through said through fluid outlet openings.

21. The insertion tube remote viewing device of claim 15, wherein said insertion tube remote viewing device further includes a thermal sensor disposed to sense a temperature of said camera head assembly and an image sensor disposed in said camera head assembly, wherein said fluid supply system is responsive to said temperature, and wherein said thermal sensor is provided by one of a dedicated temperature sensor or said image sensor.

* * * * *